United States Patent [19]
Dean et al.

[11] Patent Number: 5,464,831
[45] Date of Patent: Nov. 7, 1995

[54] THIENOTHIADIAZINE SULFONAMIDES USEFUL AS CARBONIC ANHYDRASE INHIBITORS

[75] Inventors: Thomas R. Dean, Weatherford, Tex.; Abdelmoula Namil, Cappelle en Pevéle, France

[73] Assignee: Alcon Laboratories, Inc., Fort Worth, Tex.

[21] Appl. No.: 303,900

[22] Filed: Sep. 9, 1994

[51] Int. Cl.$^6$ .................. C07D 513/04; A61K 31/54
[52] U.S. Cl. ............................. 514/222.8; 544/10
[58] Field of Search ..................... 544/10; 514/222.8

[56] References Cited

U.S. PATENT DOCUMENTS

| | | | |
|---|---|---|---|
| 4,619,939 | 10/1986 | Maren | 514/363 |
| 4,797,413 | 1/1989 | Baldwin et al. | 514/432 |
| 5,153,192 | 10/1992 | Dean et al. | 514/226.5 |
| 5,240,923 | 8/1993 | Dean et al. | 514/226.5 |
| 5,308,863 | 5/1994 | Baldwin et al. | 514/431 |

FOREIGN PATENT DOCUMENTS

91/452151A1  10/1991  European Pat. Off. .

*Primary Examiner*—John M. Ford
*Attorney, Agent, or Firm*—Sally Yeager

[57] ABSTRACT

New thienothiadiazine sulfonamides useful as carbonic anhydrase inhibitors are disclosed. Methods for using the compounds to control IOP are also disclosed.

6 Claims, No Drawings

THIENOTHIADIAZINE SULFONAMIDES USEFUL AS CARBONIC ANHYDRASE INHIBITORS

FIELD OF THE INVENTION

The present invention relates to new thienothiadiazine sulfonamides useful in lowering and controlling intraocular pressure.

BACKGROUND OF THE INVENTION

Glaucoma is a disease of the eye which is characterized by a progressive loss of visual field due to irreversible damage to the optic nerve. If untreated, this condition can result in blindness. This loss of visual field, in one form of primary open angle glaucoma, that is, chronic primary open angle glaucoma, hereinafter POAG, is associated with a sustained increase in the intraocular pressure (IOP) of the diseased eye. In addition, elevated intraocular pressure without visual field loss, or ocular hypertension, can be indicative of the early stages of POAG.

There are a number of therapies that target reducing the elevated IOP associated with ocular hypertension or POAG. The most common feature the topical administration of a beta adrenergic antagonist (beta-blocker) or a muscarinic agonist. These treatments, while effective in lowering IOP, can also produce significant undesirable side effects.

Another less common treatment for ocular hypertension or POAG is the systemic administration of carbonic anhydrase inhibitors; however, this therapy can also bring about unwanted side effects, such as nausea, dyspepsia, fatigue, and metabolic acidosis. Topical administration of carbonic anhydrase inhibitors can be used to control IOP with a reduced risk of encountering the aforementioned systemic side effects. U.S. Pat. Nos. 5,153,192; 5,240,923; 4,797,413; 5,308,863; and EPO 91/452,151A1 disclose topically dosed sulfonamides which lower IOP by inibiting carbonic anhydrase.

SUMMARY OF THE INVENTION

The present invention is directed to new thienothiadiazine sulfonamides which can be used to lower and control IOP. The compounds are formulated in pharmaceutical compositions for delivery.

The invention is also directed to methods for treating ocular hypertension and POAG by lowering and controling IOP by the administration of the thienothiadiazine sulfonamides of the present invention. The compounds can be administered systemically and/or topically to the eye.

DETAILED DESCRIPTION OF THE INVENTION

The thienothiadiazine sulfonamides of the present invention have the following structure.

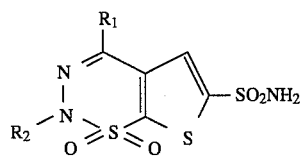

or a pharmaceutically acceptable salt thereof wherein:

$R_1$ is H; $C_{1-6}$ alkyl unsubstituted or substituted optionally with OH, $C_{1-4}$ alkoxy, $NR_3R_4$, $OC(=O)R_5$ or $C(=O)R_5$;

$R_2$ is H; $C_{1-8}$ alkyl; $C_{1-8}$ alkyl substituted with OH, $NR_3R_4$, halogen, $C_{1-4}$ alkoxy, $C_{2-4}$ alkoxy, $C_{1-4}$ alkoxy, $OC(=O)R_5$, $S(=O)_mR_7$, or $C(=O)R_5$; $C_{3-7}$ alkenyl unsubstituted or substituted optionally with OH, $NR_3R_4$, or $C_{1-4}$ alkoxy; $C_{3-7}$ alkynyl unsubstituted or substituted optionally with OH, $NR_3R_4$, or $C_{1-4}$ alkoxy; $C_{0-3}$ alkyl substituted with $R_6$ which can be unsubstituted or substituted optionally with $C_{1-3}$ alkyl, $C_{1-3}$ haloalkyl, OH, $(CH_2)_nNR_3R_4$, halogen, $C_{1-4}$ alkoxy, $C_{1-4}$ haloalkoxy, $OC(=O)R_5$, $C(=O)R_5$, $S(=O)_mR_7$ or $SO_2NR_3R_4$, wherein m is 0–2 and n is 0–2;

$R_3$ and $R_4$ are the same or different and are H; $C_{1-8}$ alkyl; $C_{2-4}$ alkyl substituted optionally with OH, halogen, $C_{1-4}$alkoxy or $C(=O)R_5$; OH; $C_{1-4}$ alkoxy; $C_{2-4}$ alkoxy substituted optionally with OH, halogen, $C_{1-4}$ alkoxy or $C(=O)R_5$; or $R_3$ and $R_4$ can be joined to form a ring of 5 or 6 atoms selected from O, S, C or N which can be unsubstituted or substituted optionally on carbon with OH, (=O), halogen, $C_{1-4}$ alkoxy, $C(=O)R_5$, $C_{1-6}$ alkyl, $C_{1-6}$ alkyl substituted optionally with OH, halogen, $C_{1-4}$ alkoxy, $C(=O)R_5$ or on nitrogen with $C_{1-4}$ alkoxy, $C(=O)R_5$, $S(=O)_mR_7$, $C_{1-6}$ alkyl or $C_{2-6}$ alkyl substituted optionally with OH, halogen, $C_{1-4}$ alkoxy, $C(=O)R_5$ or on sulfur by $(=O)_m$, wherein m is 0–2.

$R_5$ is $C_{1-8}$ alkyl; $C_{1-4}$ alkyl substituted optionally with OH, $NR_3R_4$, halogen, $C_{1-4}$ alkoxy or $C(=O)R_8$; $C_{1-4}$ alkoxy; $C_{2-4}$ alkoxy substituted optionally with OH, $NR_3R_4$, halogen or $C_{1-4}$ alkoxy; or $NR_3R_4$.

$R_6$, is a monocyclic ring system of 5 or 6 atoms composed of C, N, O and/or S, such as benzene, furan, thiophene, pyrrole, pyrazole, imidazole, triazole, tetrazole, oxazole, isoxazole, isothiazole, thiazole, thiadiazole, pyridine pyrimidine, pyridazine, and pyrazine.

$R_7$ is $C_{1-4}$ alkyl; $C_{2-4}$ alkyl substituted optionally with OH, $NR_3R_4$, $C_{1-4}$ alkoxy or $C(=O)R_5$; $R_6$ which can be unsubstituted or substituted optionally with OH, $(CH_2)_nNR_3R_4$, halogen, $C_{1-4}$ alkoxy, $C_{1-4}$ haloalkoxy, $C(=O)R_5$, $S(=O)_mC_{1-4}$ alkyl or $SO_2NR_3R_4$; wherein m is 0–2 and n is 0–2; and $R_8$ is $C_{1-4}$ alkyl; $C_{1-4}$ alkoxy; amino, $C_{1-3}$ alkylamino, of di-$C_{1-3}$ alkylamino.

In the above definitions, the total number of carbon atoms in a substituent group is indicated by the $C_{i-j}$ prefix where i and j are numbers from 1 to 8, for example. This $C_{i-j}$ definition includes both the straight and branched chain isomers. For example, $C_{1-4}$ alkyl would designate methyl through the butyl isomers and includes cyclopropylmethyl; and $C_{1-4}$ alkoxy would designate methoxy through the butoxy isomers.

The term "halogen," either alone or in compound words such as "haloalkyl," means fluorine, chlorine, bromine, or iodine. Further, when used in compound words such as "haloalkyl," said alkyl may be partially or fully substituted with halogen atoms, which may be the same or different.

The compounds are advantageous due to ease of synthesis because they do not possess chiral centers within the bicyclic nucleus.

Compounds of the present invention can be prepared using the procedures described below in reaction Schemes 1–4.

The most direct preparation of 1 can be accomplished by the selective alkylation of 1a (Scheme 1). The alkylating agents contemplated in Scheme 1 are limited by their stability and reactivity trader the reaction conditions and as such are relatively simple reagents. These alkylating agents are defined as those which will furnish directly the $R_2$ substituents of this invention. Alkylating agents of this type Scheme 1:

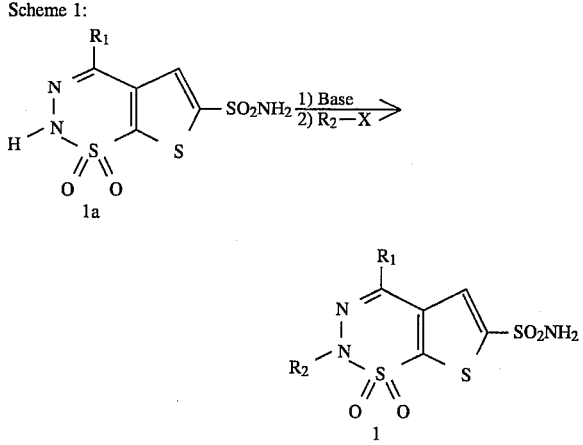

Compounds 1 are added to a solution or suspension of generally one equivalent of a strong base such as sodium hydride or potassium tert-butoxide in a polar aprotic solvent such as N,N-dimethylformamide (DMF) or dimethylsulfoxide (DMSO) or similar solvent at temperatures ranging from 0° C. to 25° C. The mixture is allowed to stir until the deprotonation is judged to be complete. Under these conditions the cyclic sulfonylhydrazone moiety is believed to be selectively deprotonated. The alkylating agent is added to the mixture and the reaction is allowed to stir at temperatures ranging from ambient to 100° C. When the reaction is judged to be complete using a variety of methods such as a thin layer chromatography (TLC), high pressure liquid chromatography (HPLC), gas chromatography (GC), or other similar means well known to one skilled in the art, the reaction mixture is poured onto water, extracted, washed, dried, and concentrated to yield the crude product. The final purification is accomplished by recrystallization, flash chromatography or by conversion (where appropriate) to a salt form and crystallized. The $R_2$–X groups useful in Scheme 1 are defined as follows: X is selected from Cl, Br, I, O-p-Tosylate, O-mesylate or a similar leaving group; $R_2$ is $C_{1-8}$ alkyl; $C_{3-7}$ alkenyl; $C_{3-7}$ alkynyl; $C_{1-3}$ alkyl substituted optionally with $C_{1-4}$ alkoxy, $C_{2-4}$ alkoxy, $C_{1-4}$ alkoxy, O(C=O)$R_5$, $SR_7$ or C(=O)$R_5$; $C_{1-3}$ alkyl substituted with $R_6$; and $R_5$, $R_6$, and $R_7$, are as previously defined. In the cases where the alkylating agent precursors of the desired $R_2$ substituents of this invention are not acceptable for this method, the alternative procedure shown in Scheme 2 can be used.

Compounds 1 with complex $R_2$ substituents can be prepared according to Scheme 2. This reaction sequence features the reaction of 1b with nucleophilic reagents, which furnish the target $R_2$ substituents found in 1 (Equation 2a). The nucleophic reagents useful in this scheme for example include a wide variety of amines, alkoxides and thioalkoxides all of which are included in the definition of the $R_2$ substituent in 1. This method is very straight forward and one skilled in the art is well versed in the specific reaction conditions required for each type of nucleophile used. 1b is prepared using the methods described in Schemes 2b and 2c.

1b can be prepared by the alkylation of 2 with special alkylating agents (Schemes 2b and 2c). These special alkylating agents are generally thought of as bis-electrophiles or masked bis-electophiles by those skilled in the art. For example 1,2-dibromoethane and 1,3-dibromopropane are representative of biselectrophiles and 1-bromo-3-acetoxypropane is an example of a masked biselectrophile. The term "masked" is thought of as a functional group which will not interfere with the first alkylation reaction but can be readily transformed into a good leaving group. In the case of 1-bromo-3-acetoxypropane, for example, the acetate group is the "masked" electrophile as it can be converted into a good leaving group at a later step. In this general method, 2 is alkylated with these special alkylating agents to give 1b in a manner similar to that described in Scheme 1. When a bis-electrophile is used as the alkylating agent 1b is directly treated with another nucleophilic reagent to yield 1 (Scheme 2a). When a masked electrophile is employed (Scheme 2c), the first step is analogous to Scheme 2b. The second step involves the "unmasking" procedure and subsequent conversion into a suitable leaving group (Scheme 2c).

Scheme 2a:

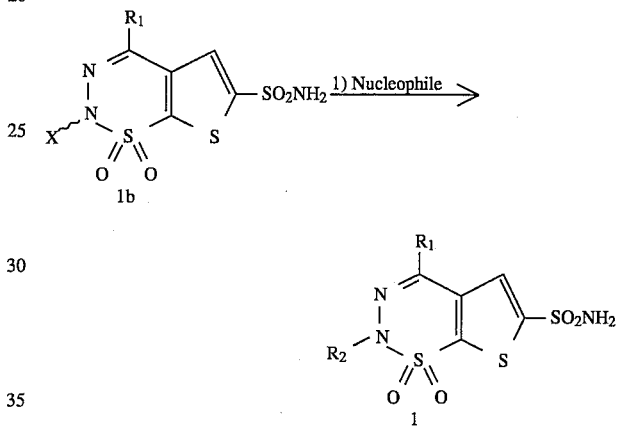

Scheme 2b:

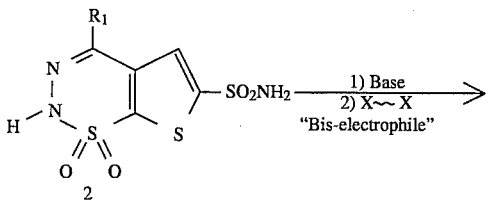

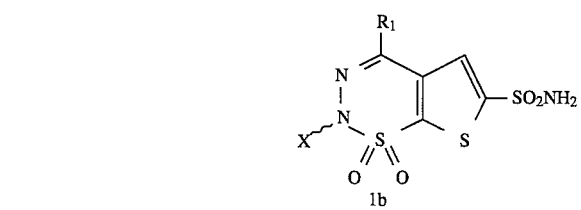

Scheme 2c:

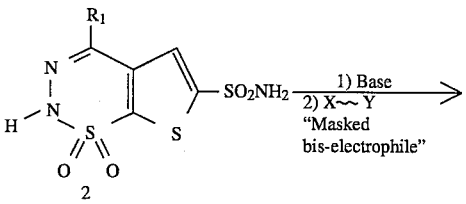

-continued

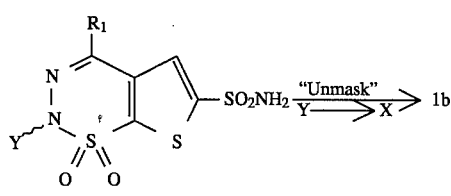

In Scheme 2 the base, bis-electrophile and masked bis-electrophile are defined as follows: The base used in equation b can be a wide variety of reagents such as those described in Scheme 1 and $K_2CO_3$, $Na_2CO_3$, NaOH, KOH, and other similar substances. The solvent used in this step is generally similar to that described in Scheme 1. X is as defined in Scheme 1. The "tether" joining the two X groups in equation b or the X and Y groups in equation c is defined as a $C_{2-8}$ alkyl chain, a $C_{3-7}$ alkenyl chain and a $C_{3-7}$ alkynyl group where the X or Y group are attached to the primary carbon. Y is defined as any group which will serve as an immediate precursor to a leaving group, including alcohols, or protected alcohols, esters, amides and similar functionalities. The types of groups useful in this capacity would be well known to one skilled in the art.

1a can be prepared according to Scheme 3. This method features the introduction of the key primary sulfonamide moiety either by step 1) deprotonation or transmetallation reaction of 4 (Z=H or Cl) and step 2) condensation with sulfur dioxide and step 3) reaction of the lithium sulfinate salt with hydroxylamine-O-sulfonic acid. Alternatively, step 3 can be modified to: step 3a) reaction of the lithium sulfinate salt with N-chlorosucciniimide or chlorine gas to furnish the corresponding sulfonyl chloride; and step 3b) amination with liquid ammonia to furnish 1a. In some cases it is more desirable to use t-butylamine in step 4 instead of ammonia. This serves as a protecting group, which can be removed later by the action of trifluoroacetic acid.

Scheme 3:

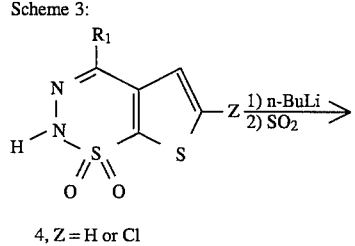

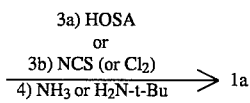

The bicyclic ring system of compounds of 4 (Z=H) can be constructed according to Scheme 4. This method takes advantage of the effect of an acetal or ketal moiety attached to the 3-position of 5 to direct lithation to the 2-position of the thiophene nucleus (Equation 4a). These anions are then trapped with $SO_2$ and the resultant sulfinated salt converted to 4 using known methods. The preparation of 4 where Z=Cl can be accomplished according to Scheme 4b. In this instance, thiol ether derivatives of 6 are used to introduce the sulfonyl hydrazide via a process involving oxidative chlorination followed by the addition of hydrazine. The intermediate sulfonyl hydrazides are cyclized to 4 using methods outlined in equation 4a.

Scheme 4a:

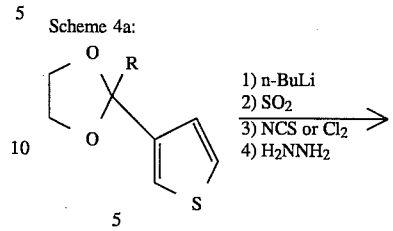

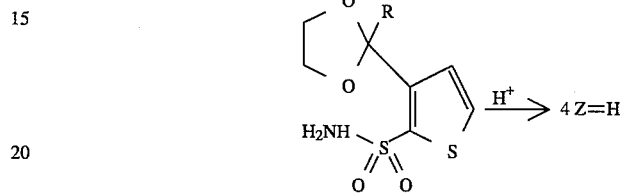

Scheme 4b:

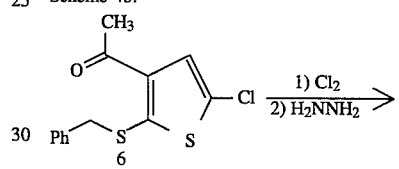

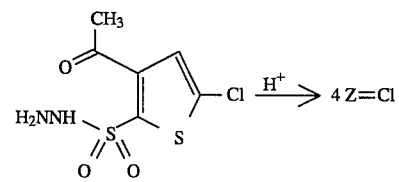

The compounds of the present invention can be incorporated into various types of ophthalmic formulations for delivery to the eye. These compounds may be combined with ophthalmologically acceptable preservatives, surfactants, viscosity enhancers, penetration enhancers, buffers, sodium chloride, and water to form an aqueous, sterile ophthalmic suspension or solution. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, Carbopolo-940 or the like according to the published formulations for analogous ophthalmic preparations; preservatives and tonicity agents can be incorporated. Ophthalmic solution formulations may be prepared by dissolving the active ingredient in a physiologically acceptable isotonic aqueous buffer. Further, the ophthalmic solution may include an ophthalmologically acceptable surfactant to assist in dissolving the active ingredient. A thickener, such as hydroxymethylcellulose, hydroxypropylmethylcellulose, methylcellulose, polyvinylpyrrolidone, or the like, to improve the retention of the medicament in the conjunctival sac.

The compounds are preferably formulated as topical ophthalmic suspensions or solutions, with a pH of about 4.5 to 8.0. The compounds will normally be contained in these formulations in an amount of 0.1% to 10% by weight, but preferably in an amount of 0.25% to 5.0% by weight. Thus, for topical presentation these formulations would be delivered to the surface of a mammal's eye 1 to 3 times a day according to the routine discretion of a skilled clinician.

The following examples, which are in no way limiting, illustrate the preparation of selected examples of the compounds of the present invention. The compotmd set forth in Examples 2 and 4 represents the preferred thienothiadiazine sulfonamides.

EXAMPLE 1

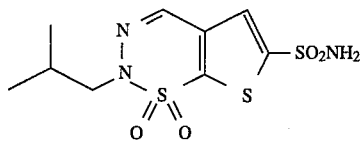

2-(2-Methylpropyl)-2H-thieno[3,2-e]-1,2,3-thiadiazine-6-sulfonamide 1,1-dioxide

Scheme 1

Step A: 3-(1,3-dioxan-2-yl)-2-thiophenesulfonic acid hydrazide

To a solution of 3-(1,3-dioxan-2-yl) thiophene (3.6 g, 23 mmol) in dry THF (40 mL) at −78° C. was added dropwise n-butyllithium (2.5 M in hexanes, 10.15 mL, 25 mmol). After stirring at −78° C. for 1h, a stream of sulfur dioxide was passed through the surface of the mixture for 15 min then the mixture was allowed to warm to room temperature. The solvent was evaporated to give a residue which was dried in vacuo. This was dissolved in methylene chloride (60 mL) and cooled to 0° C. N-chlorosuccinimide (3.99 g, 29 mmol) was added. The mixture was allowed to warm to room temperature and stirred for 2h then the THF was evaporated. The oil obtained was diluted with water (80 mL), extracted with ethyl acetate (3×30 mL), ethyl acetate fractions were combined, dried over MgSO$_4$ and evaporated to give the sulfonyl chloride intermediate as a brown oil. The sulfonyl chloride was dissolved in THF and then added to a cold solution of hydrazine in THF (−10° C.). After 15 min the mixture was allowed to warm to room temperature and stirred for 2h. THF was evaporated and the residue obtained was diluted with water (50 mL) and extracted with ethyl acetate (2×50 mL), the combined extracts were washed with brine (100 mL), dried over MgSO$_4$ and evaporated to give a yellow solid (2.5 g, 43%). Cl-MS m/e 250 (M+H)$^+$. $^1$H NMR (DMSO-d$_6$): δ:4.30 (4H, m, 2CH$_2$); 6.24 (1H, 1s, CH); 7.17 (1H, d, J=5.2 Hz); 7.75 (1H, d, J=5.2 Hz).

Step B: 2H-Thieno[3,2-e]-1,2,3-thiadiazine-1,1-dioxide

The solid obtained in step A (2.4 g, 48 mmol) was dissolved in acetone (70 mL). p-Toluenesulfonic acid (0.20 g, 1 mmol) was added and the mixture was stirred at refluxing temperature (56° C.) for 2h. The solvent was evaporated, the residue obtained was dissolved in ethyl acetate, washed with saturated aqueous sodium bicarbonate (20 mL) and brine. The ethyl acetate layer was dried over MgSO$_4$ and evaporated to a green solid which was flash chromatographed (silica, hexane-ethyl acetate gradient) to provide a white solid (1.62 g, 90%). mp:125°–127° C. Cl-MS m/e 189 (M+H)$^+$. $^1$HNMR (DMSO-d$_6$):δ:7.44 (1H, 1s, CH); 7.44 (1H, d, J=5.0 Hz); 8.05 (1H, d, J=5.0 Hz); 8.24 (1H, 1s , CH=N). 13C NMR (DMSO-d$_6$) δ 2125.96, 132.00, 133.64, 136.96, 137.12.

Step C: 2H-Thieno[3,2-e]-1,2,3-thiadiazine-6-sulfonamide 1,1-dioxide

The product from step B (0.1 g, 5.3 mmol) was dissolved in dry THF (4 mL) and cooled to −78° C. under nitrogen. n-Butyllithium (0.7 mL of a 2.5 M solution in hexanes, 1.75 mmol) was added dropwise, the mixture stirred for 1h at −78° C. A stream of sulfur dioxide gas was passed through the surface of the mixture for 15 min. and then the mixture was allowed to warm to room temperature. Evaporation of the reaction mixture provided a residue which was dissolved in water (5 mL) to which was added sodium acetate trihydrate (0.21 g, 1.39 mmol); this solution was cooled to 0° C. and hydroxylamine-O-sulfonic acid (0.18 g, 1.39 mmol) was added followed by stirring for 18 h. The reaction mixture was extracted with ethyl acetate (2×5 mL). The combined extracts were dried over MgSO$_4$ and concentrated to a crude oil which was purified by flash column chromatography (silica, hexane-ethyl acetate gradient) to give a white solid. (0.021 g, 15%). decomposition:t>183° C. Cl-MS m/e 268 (m+H)$^+$. $^1$HNMR (DMSO-d$_6$):δ :7.90 (1H, 1s, CH); 8.22 (2H, S, NH$_2$ exchangeable); 8.34 (1H, 1s, CH=N).

Step D: 2-(2-Methylpropyl)-2H-thieno[3,2-e]-1,2,3-thiadiazine-6-sulfonamide 1,1-dioxide The product from step C (0.05 g, 0.18 mmol) was dissolved in DMF (1 mL). Sodium hydride (0.016 g, 40 mmol of a 60% suspension in mineral oil) was added slowly at room temperature. The mixture was stirred for 15 min and then 2-methylbromopropane (0.024 mL, 0.40 mmol) was added. The mixture was warmed to 60° C. and stirred for 12h. DMF was evaporated under high vacuum. The residue obtained was diluted with water (1 mL) and the mixture was extracted with ethyl acetate (3×1 mL). The combined extracts were dried over MgSO$_4$ and evaporated to provide an oil which was purified by flash column chromatography (silica, hexane-ethyl acetate gradient) to give the desired compound as a white solid, crystallization in ethyl acetate-hexane gave 0.032 g (52%). mp:130°–132° C. $^1$HNMR (CDCl$_3$):δ:0.96 (6H, d, 2CH$_3$); 2.18 (1H, m, CH); 3.78 (2H, d, CH$_2$); 5.27 (2H, s, NH$_2$ exchangeable); 7.67 (1H, 1s, CH); 7.91 (1H, s, CH=N). Analysis calculated for C$_9$H$_{13}$N$_3$O$_4$S$_3$: C, 33.42; H, 4.05; N, 12.99. Found: C, 33.51; H, 4.04; N, 12.91.

EXAMPLE 2

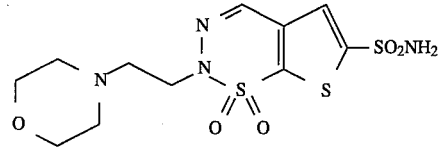

2-[2-(4-Morpholinyl)ethyl]-2H-thieno[3,2-e]-1,2,3-thiadiazine-6-sulfonamide 1,1-dioxide The product from step C (1.00 g, 3.74 mmol) was dissolved in DMF (13 mL). Sodium hydride (0.57 g, 14.23 mmol of a 60% suspension in mineral oil) was added slowly at room temperature. The mixture was stirred for 15 min and then chloroethylmorpholine hydrochloride salt (1.39 g, 7.5 mmol) was added. The mixture was warmed to 50° C. and stirred for 12h then warmed to 80° C. and stirred for 1h. DMF was evaporated under high vacuum. The residue obtained was diluted with water (10 mL) and the mixture was extracted with ethyl acetate (3×10 mL). The combined extracts were dried over MgSO$_4$ and evaporated to provide a brown oil which was purified twice by flash column chromatography (silica, hexane-ethyl acetate gradient) to give the desired compound as a white solid. Crystallization in ethyl acetate-hexane gave 0.1 g, (9%). mp: 164°–166° C. $^1$HNMR (DMSO-d$_6$): δ:2.46 (4H, m, 2CH$_2$N); 2.155 (2H, t, CH$_2$); 3.45 (4H, m, 2CH$_2$O); 4.01 (2H, t, CH$_2$); 7.91 (1H, 1s, CH); 8.30 (2H, s, NH$_2$ exchangeable), 8.43 (1H, s, CH=N). Analysis calculated for C$_{11}$H$_{16}$N$_4$O$_5$S$_3$–0.15 Ethyl acetate: C, 35.39; H, 4.40; N, 14.23. Found: C, 35.60; H, 4.39; N, 13.96.

EXAMPLE 3

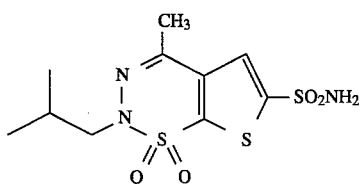

4-Methyl-2-(2omethylpropyl)-2H-thieno[3,2-e]-1,2,3-thiadiazine-6-sulfonamide 1,1-dioxide Scheme 2:

Step A: 6-Chloro-4-methyl-2H-thieno[3,2-e]-1,2,3-thiadiazine 1,1-dioxide

To a stirred suspension of S-benzyl-3-acetyl-5 chloro-2-mercaptothiophene (10.42 g, 36.8 mmol) in acetic acid-water (v/v 200 mL), was bubbled chlorine gas at 0° C. The mixture was stirred for 1h. The excess of chlorine was flashed off with a stream of N$_2$ and then water (100 mL) was added. This was extracted with ethyl acetate (4×100 mL) and the combined extracts were washed with brine (3×100 mL) and carefully washed with aqueous solution of sodium bicarbonate 10% (4×100 mL). The ethyl acetate layer was dried over MgSO$_4$ and evaporated. The crude was dissolved in THF (100 mL) and added dropwise to a cold solution (−10° C.) of hydrazine monohydrate (3.57 g, 73.3 mL) in THF (200 mL). After 15 min the mixture was allowed to warm to room temperature and stirred for 2h. THF was evaporated and the residue obtained was diluted with water (100 mL) and extracted with ethyl acetate (2×100 mL). The combined extracts were washed with brine (100 mL), dried over MgSO$_4$ and evaporated to give a yellow solid. This was purified by flash chromatography on silica (hexane-ethyl acetate gradient) to give a white solid. (2 g, 30%). mp: 182°–184° C. $^1$HNMR (DMSO-d$_6$): δ :2.38 (3H, 1s, CH$_3$), 7.68 (1H, 1s, CH=N). Analysis calculated for C$_6$H$_5$N$_2$O$_2$S$_2$Cl: C, 30.45; H, 2.13; N, 11.83. Found: C, 30.59; H, 2.14; N, 11.75.

Step B: 4-Methyl-2H-thieno[3,2-e]-1,2,3-thiadiazine-6-sulfonamide 1,1-dioxide

The product from step A (1.5 g, 6.30 mmol) was dissolved in dry THF (60 mL) and cooled to −78° C. under nitrogen. n-Butyllithium (5.33 mL of a 2.5 M solution in hexanes, 13.3 mmol) was added dropwise and the mixture was stirred for 1h at −78° C. A stream of sulfur dioxide gas was passed through the surface of the mixture for 15 min and then the mixture was allowed to warm to room temperature. Evaporation of the volatiles provided a residue which was dissolved in water (60 mL) to which was added sodium acetate trihydrate (2.59 g, 19.06 mmol). This solution was cooled to 0° C. and hydroxylamine-O-sulfonic acid (2.15 g, 19.06 mmol) was added followed by stirring for 18h. The reaction mixture was extracted with ethyl acetate (2×50 mL). The combined extracts were dried over MgSO$_4$ and concentrated to a crude oil which was purified by flash column chromatography (silica, hexane-ethyl acetate gradient) to lead to a white solid (1 g, 50%). decomposition: >163° C. $^1$H NMR (DMSO-d$_6$): δ:2.48 (3H, 1s, CH$_3$); 8.17 (2H, s, NH$_2$ exchangeable).

Step C: 4-Methyl-2-(2-methylpropyl)-2H-thieno[3,2-e]-1,2,3-thiadiazine-6-sulfonamide 1,1-dioxide The product from step B (0.9 g, 2.85 mmol) was dissolved in DMF (10 mL). Sodium hydride (0.17 g, 4.28 mmol of a 60% suspension in mineral oil) was added slowly at room temperature. The mixture was stirred for 15 min and then 2-methyl bromopropane (0.47 mL, 4.28 mmol) was added. The mixture was warmed to 80° C. and stirred for 2h. And then cooled to 0° C. and stirred for 12h. DMF was evaporated under high vacuum. The residue obtained was diluted with water (20 mL) and extracted with ethyl acetate (3×20 mL). The combined extracts were dried over MgSO$_4$ and evaporated to provide an oil which was purified by flash column chromatography (silica, hexane-ethyl acetate gradient) to give the desired compound as a white solid (0.54 g, 50%). mp: 140°–142° C. $^1$H NMR (DMSO-d$_6$): δ:0.89 (6H, d, 2CH$_3$); 2.03 (1H, m, CH); 2.49 (3H, s, CH$_3$); 3.64 (2H, δ, CH$_2$); 7.94 (1H, s, CH); 8.21 (2H, s, NH$_2$ exchangeable). Analysis calculated for C$_9$H$_{13}$N$_3$O$_4$S$_3$: C, 35.59; H, 4.78; N, 12.45 Found: C, 35.56; H, 4.44; N, 12.36.

EXAMPLE 4

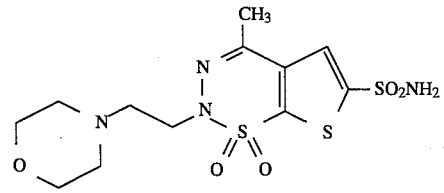

2-[2-(4-Morpholinyl)ethyl]-4-methyl-2H-thieno[3,2-e]-1,2,3-thiadiazine-6-sulfonamide 1,1-dioxide The product from step C Example 1 (2.83 g, 10.07 mmol) was dissolved in DMF (40 mL). Sodium hydride (1.2 g, 30.21 mmol of a 60% suspension in mineral oil) was added slowly at room temperature. The mixture was stirred for 15 min and then chloroethylmorpholine hydrochloride salt (3.74 g, 20.14 mmol) was added. The mixture was warmed to 70° C. and stirred for 1h. DMF was evaporated under high vacuum. The residue obtained was diluted with 1N-HCl (50 mL) and washed with ethyl acetate (2×50 mL). The aqueous layer was neutralized with aqueous solution bicarbonate and extracted with ethyl acetate (3×50 mL). The combined ethyl acetate fractions were dried over MgSO$_4$ and evaporated to provide a solid, repeated recrystallization from ethyl acetate-hexane yielded 1.35 g, (71%). mp: 160°–162° C. $^1$H NMR (DMSO-d$_6$): δ: 2.38 (3H, s, CH$_3$); 2.50 (4H, m, 2CH$_2$N); 2.64 (2H, t, CH$_2$); 3.50 (4H, m, 2CH$_2$O); 4.01 (2H, t, CH$_2$); 7.94 (1H, 1s , CH); 8.22 (2H, s, NH$_2$ exchangeable). Analysis calculated for C$_{12}$H$_{18}$N$_4$O$_5$S$_3$-0.15 Ethyl acetate: C, 37.12; H, 4.74; N, 13.74. Found: C, 37.10; H, 4.79; N, 13.90.

EXAMPLE 5

Ophthalmic Suspension

| Ingredient | Concentration (wt %) |
| --- | --- |
| 2-[2-(4-Morpholinyl)ethyl]-2H-thieno[3,2-e]-1,2,3-thiadiazine-6-sulfonamide 1,1-dioxide (Compound) | 3.0% |
| Hydroxypropylmethylcellulose | 0.5% |
| Dibasic Sodium Phosphate | 0.2% |
| Disodium Edetate | 0.01% |
| Sodium Chloride | 0.8% |
| Purified Water | q.s |
| Benzalkonium Chloride | 0.01% |
| Polysorbate 80 | 0.1% |
| NaOH/HCl | pH 7.02 |

The Compound (0.09 g), benzalkonium chloride (0.03 g) and, polysorbate 80 (0.15 g) can be mixed together in water (1.23 g) and ball milled for approximately 4 h. A hydroxypropylmethylcellulose vehicle can be prepared by mixing 2% aqueous hydroxypropylmethylcellulose (40 g), sodium chloride (1.28 g), dibasic sodium phosphate (0.32 g), disodium edetate (0.016 g), sodium chloride (1.28 g) and water (35 g) together and the pH adjusted to 7.4 by the addition of 1N HCl (250 µL). A portion of this vehicle (1.5 mL) can be added to the mixture containing the Compound to furnish the desired suspension.

EXAMPLE 6

Ophthalmic Solution

| Ingredient | Concentration (wt %) |
| --- | --- |
| 2-[2-(4-Morpholinyl)ethyl]-2H-thieno[3,2-e]-1,2,3-thiadiazine-6-sulfonamide 1,1-dioxide (Compound) | 2.0% |
| Hydroxyethylcellulose | 0.5% |
| Monobasic Sodium Phosphate | 0.13% |
| Dibasic Sodium Phosphate | 0.01% |
| Benzalkonium Chloride | 0.01% |
| Disodium Edetate | 0.01% |
| Purified Water | q.s. |
| NaCl (Osmolality = 282 mOsm) | 0.4% |
| HCl/NaOH | pH 5.0 |

The Compound (0.06 g) and sodium chloride (0.014 g) can be mixed together in water (1.44 g) and the pH of the solution is adjusted to 5.02 by the addition of 1N NaOH (10 µL). The hydroxyethylcellulose vehicle is then prepared by mixing together monobasic sodium phosphate (0.26 g), dibasic sodium phosphate (0.02 g) and disodium edetate (0.02 g) in water (96.7 g). The benzalkonium chloride (2.0 g) and hydroxyethylcellulose are added to the mixture and the pH is adjusted to 5.01 by the addition of 1N HCl (100 µl). A portion of this vehicle (1.5 g) is added to the solution containing the compound and the pH is adjusted to 5.03 by the addition of 1N NaOH (10 µL).

EXAMPLE 7

Ophthalmic Gel

| Ingredient | Concentration (wt %) |
| --- | --- |
| 2-[2-(4-Morpholinyl)ethyl]-4-methyl-2H-thieno[3,2-e]-1,2,3-thiadiazine-6-sulfonamide 1,1-dioxide (Compound) | 1.0% |
| Mannitol | 3.6% |
| Benzalkonium Chloride | 0.01% |
| Carbopol | 3.0% |
| HCl/NaOH | pH 5.0 |
| Purified Water | q.s. |

The mannitol (0.18 g), benzalkonium chloride (0.05 mL), Compound (0.1 g) and carbopol (0.15 g) can all be added to water (4.3 mL) and mixed well. The pH can be adjusted to pH 5.0 and purified water (q.s. to 5 mL) can be added and mixed well to form a gel.

EXAMPLE 8

Ophthalmic Suspension

| Ingredient | Concentration (wt %) |
| --- | --- |
| 2-[2-(4-Morpholinyl)ethyl]-4-methyl-2H-thieno[3,2-e]-1,2,3-thiadiazine-6-sulfonamide 1,1-dioxide (Compound) | 2.0% |
| Carbomer 934P | 0.5% |
| Sodium Chloride | 0.4% |
| Mannitol | 2.4% |
| Disodium EDTA | 0.01% |
| Polysorbate 80 | 0.05% |
| Benzalkonium Chloride Solution | 0.01% + 5% xs |
| Sodium Hydroxide | q.s. pH = 7.2 |
| Hydrochloric Acid | q.s. pH = 7.2 |
| Water for Injection | q.s. 100% |

The above ingredients can be mixed together using a method similar to the same general procedure described in Example 5 to furnish the ophthalmic suspension.

EXAMPLE 9

Ophthalmic Suspension

| Ingredient | Concentration (wt %) |
| --- | --- |
| 2-[2-(4-Morpholinyl)ethyl]-2H-thieno[3,2-e]-1,2,3-thiadiazine-6-sulfonamide 1,1-dioxide (Compound) | 2.0% |
| Carbomer 934P | 0.5% |
| Sodium Chloride | 0.4% |
| Mannitol | 2.4% |
| Disodium EDTA | 0.01% |
| Polysorbate 80 | 0.05% |
| Benzalkonium Chloride Solution | 0.01% + 5% xs |
| Sodium Hydroxide | q.s. pH = 7.2 |
| Hydrochloric Acid | q.s. pH = 7.2 |
| Water for Injection | q.s. 100% |

The above ingredients can be mixed together using a method similar to the same general procedure described in Example 5 to furnish the ophthalmic suspension.

We claim:

1. A compound having the following structure:

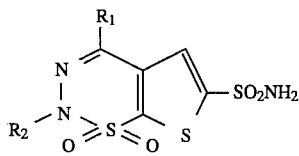

or a pharmaceutically acceptable salt thereof wherein:

$R_1$ is H; $C_{1-8}$ alkyl unsubstituted or substituted optionally with OH, $C_{1-4}$ alkoxy, $NR_3R_4$, $OC(=O)R_5$ or $C(=O)R_5$;

$R_2$ is H; $C_{1-8}$ alkyl $C_{1-8}$ alkyl substituted with OH, $NR_3R_4$, halogen, $C_{1-4}$ alkoxy, $C_{2-4}$ alkoxy, $C_{1-4}$ alkoxy, $OC(=O)R_5$, $S(=O)_mR_7$, or $C(=O)R_5$; $C_{3-7}$ alkenyl unsubstituted or substituted optionally with OH, $NR_3R_4$, or $C_{1-4}$ alkoxy; $C_{3-7}$ alkynyl unsubstituted or substituted optionally with OH, $NR_3R_4$, or $C_{1-4}$ alkoxy; $C_{0-3}$ alkyl substituted with $R_6$ which can be unsubstituted or substituted optionally with $C_{1-3}$ alkyl, $C_{1-3}$ haloalkyl, OH, $(CH_2)_nNR_3R_4$, halogen, $C_{1-4}$ alkoxy, $C_{1-4}$ haloalkoxy, $OC(=O)R_5$, $C(=O)R_5$, $S(=O)_mR_7$ or $SO_2NR_3R_4$, wherein m is 0–2 and n is 0–2;

$R_3$ and $R_4$ are the same or different and are H; $C_{1-8}$ alkyl; $C_{2-4}$ alkyl substituted optionally with OH, halogen, $C_{1-4}$ alkoxy or $C(=O)R_5$; OH; $C_{1-4}$ alkoxy; $C_{2-4}$ alkoxy substituted optionally with OH, halogen, $C_{1-4}$ alkoxy or $C(=O)R_5$; or $R_3$ and $R_4$ can be joined to form a ring of 5 or 6 atoms selected from O, S, C or N which can be unsubstituted or substituted optionally on carbon with OH, (=O), halogen, $C_{1-4}$ alkoxy, $C(=O)R_5$, $C_{1-6}$ alkyl, $C_{1-6}$ alkyl substituted optionally with OH, halogen, $C_{1-4}$ alkoxy, $C(=O)R_5$ or on nitrogen with $C_{1-4}$ alkoxy, $C(=O)R_5$, $S(=O)_mR_7$, $C_{1-6}$ alkyl or $C_{2-6}$ alkyl substituted optionally with OH, halogen, $C_{1-4}$ alkoxy, $C(=O)R_5$ or on sulfur by $(=O)_m$, wherein m is 0–2;

$R_5$ is $C_{1-8}$ alkyl; $C_{1-4}$ alkyl substituted optionally with OH, $NR_3R_4$, halogen, $C_{1-4}$ alkoxy or $C(=O)R_8$; $C_{1-4}$ alkoxy; $C_{2-4}$ alkoxy substituted optionally with OH, $NR_3R_4$, halogen or $C_{1-4}$ alkoxy; or $NR_3R_4$.

$R_6$ is a monocyclic ring system of 5 or 6 atoms composed of C, N, O and/or S, selected from the group consisting of benzene, furan, thiophene, pyrrole, pyrazole, imidazole, triazole, tetrazole, oxazole, isoxazole, isothiazole, thiazole, thiadiazole, pyridine pyrimidine, pyridazine, and pyrazine;

$R_7$ is $C_{1-4}$ alkyl; $C_{2-4}$ alkyl substituted optionally with OH, $NR_3R_4$, $C_{1-4}$ alkoxy or $C(=O)R_5$; $R_6$ which can be unsubstituted or substituted optionally with OH, $(CH_2)_nNR_3R_4$, halogen, $C_{1-4}$ alkoxy, $C_{1-4}$ haloalkoxy, $C(=O)R_5$, $S(=O)_mC_{1-4}$ alkyl or $SO_2NR_3R_4$; wherein m is 0–2; and n is 0–2; and $R_8$ is $C_{1-4}$ alkyl; $C_{1-4}$ alkoxy; amino, $C_{1-3}$ alkylamino, of di-$C_{1-3}$ alkylamino.

2. The compound of claim 1 selected from the group consisting of:
2-[4-(2-Morpholinoethyl)]-2H-thieno[3,2-e]-1,2,3-thiadiazine-6-sulfonamide 1,1dioxide; and
2-[4-(2-Morpholinylethyl)]-4-methyl-2H-thieno[3,2-e]-1,2,3-thiadiazine-6-sulfonamide 1,1-dioxide.

3. A composition for lowering and controlling IOP comprising a pharmaceutically effective amount of a compound having the following structure:

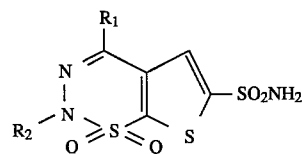

or a pharmaceutically acceptable salt thereof wherein:

$R_1$ is H; $C_{1-6}$ alkyl unsubstituted or substituted optionally with OH, $C_{1-4}$ alkoxy, $NR_3R_4$, $OC(=O)R_5$ or $C(=O)R_5$;

$R_2$ is H; $C_{1-8}$ alkyl; $C_{2-8}$ alkyl substituted with OH, $NR_3R_4$, halogen, $C_{1-4}$ alkoxy, $C_{2-4}$ alkoxy, $C_{1-4}$ alkoxy, $OC(=O)R_5$, $S(=O)_mR_7$, or $C(=O)R_5$; $C_{3-7}$ alkenyl unsubstituted or substituted optionally with OH, $NR_3R_4$, or $C_{1-4}$ alkoxy; $C_{3-7}$ alkynyl unsubstituted or substituted optionally with OH, $NR_3R_4$, or $C_{1-4}$ alkoxy; $C_{0-3}$ alkyl substituted with $R_6$ which can be unsubstituted or substituted optionally with $C_{1-3}$ alkyl, $C_{1-3}$ haloalkyl, OH, $(CH_2)_nNR_3R_4$, halogen, $C_{1-4}$ alkoxy, $C_{1-4}$ haloalkoxy, $OC(=O)R_5$, $C(=O)R_5$, $S(=O)_mR_7$ or $SO_2NR_3R_4$, wherein m is 0–2 and n is 0–2;

$R_3$ and $R_4$ are the same or different and are H; $C_{1-8}$ alkyl; $C_{2-4}$ alkyl substituted optionally with OH, halogen, $C_{1-4}$ alkoxy or $C(=O)R_5$; OH; $C_{1-4}$ alkoxy; $C_{2-4}$ alkoxy substituted optionally with OH, halogen, $C_{1-4}$ alkoxy or $C(=O)R_5$; or $R_3$ and $R_4$, can be joined to form a ring of 5 or 6 atoms selected from O, S, C or N which can be unsubstituted or substituted optionally on carbon with OH, (=O), halogen, $C_{1-4}$ alkoxy, $C(=O)R_5$, $C_{1-6}$ alkyl, $C_{1-6}$ alkyl substituted optionally with OH, halogen, $C_{1-4}$ alkoxy, $C(=O)R_5$ or on nitrogen with $C_{1-4}$ alkoxy, $C(=O)R_5$, $S(=O)_mR_7$, $C_{1-6}$ alkyl or $C_{2-6}$ alkyl substituted optionally with OH, halogen, $C_{1-4}$ alkoxy, $C(=O)R_5$ or on sulfur by $(=O)_m$, wherein m is 0–2;

$R_5$ is $C_{1-8}$ alkyl; $C_{1-4}$ alkyl substituted optionally with OH, $NR_3R_4$, halogen, $C_{1-4}$ alkoxy or $C(=O)R_8$; $C_{1-4}$ alkoxy; $C_{2-4}$ alkoxy substituted optionally with OH, $NR_3R_4$, halogen or $C_{1-4}$ alkoxy; or $NR_3R_4$;

$R_6$ is a monocyclic ring system of 5 or 6 atoms composed of C, N, O and/or S, selected from the group consisting of benzene, furan, thiophene, pyrrole, pyrazole, imidazole, triazole, tetrazole, oxazole, isoxazole, isothiazole, thiazole. thiadiazole, pyridine pyrimidine, pyridazine, and pyrazine;

$R_7$ is $C_{1-4}$ alkyl; $C_{2-4}$ alkyl substituted optionally with OH, $NR_3R_4$, $C_{1-4}$ alkoxy or $C(=O)R_5$; $R_6$ which can be unsubstituted or substituted optionally with OH, $(CH_2)_nNR_3R_4$, halogen, $C_{1-4}$ alkoxy, $C_{1-4}$ haloalkoxy, $C(=O)R_5$, $S(=O)_mC_{1-4}$ alkyl or $SO_2NR_3R_4$; wherein m is 0–2 and n is 0–2; and $R_8$ is $C_{1-4}$ alkyl; $C_{1-4}$ alkoxy; amino, $C_{1-3}$ alkylamino, of di-$C_{1-3}$ alkylamino.

4. The composition of claim 3 wherein the compound is selected from the group consisting of:
2-[4-(2-Morpholinoethyl)]-2H-thieno[3,2-e]-1,2,3-thiadiazine-6-sulfonamide 1,1-dioxide; and
2-[4-(2-Morpholinylethyl)]-4-methyl-2H-thieno[3,2-e]-1,2,3-thiadiazine-6-sulfonamide 1,1-dioxide.

5. A method for lowering and controlling IOP by administering a pharmaceutically effective amount of a compound having the following structure:

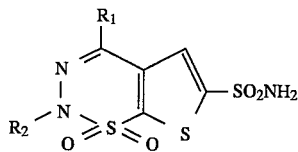

or a pharmaceutically acceptable salt thereof wherein:

$R_1$ is H; $C_{1-6}$ alkyl unsubstituted or substituted optionally with OH, $C_{1-4}$ alkoxy, $NR_3R_4$, $OC(=O)R_5$ or $C(=O)R_5$;

$R_2$ is H; $C_{1-8}$ alkyl; $C_{2-8}$ alkyl substituted with OH, $NR_3R_4$, halogen, $C_{1-4}$ alkoxy, $C_{2-4}$ alkoxy, $C_{1-4}$ alkoxy, $OC(=O)R_5$, $S(=O)_mR_7$, or $C(=O)R_5$; $C_{3-7}$ alkenyl unsubstituted or substituted optionally with OH, $NR_3R_4$, or $C_{1-4}$ alkoxy; $C_{3-7}$ alkynyl unsubstituted or substituted optionally with OH, $NR_3R_4$, or $C_{1-4}$ alkoxy; $C_{0-3}$ alkyl substituted with $R_6$ which can be unsubstituted or substituted optionally with $C_{1-3}$ alkyl, $C_{1-3}$ haloalkyl, OH, $(CH_2)_nNR_3R_4$, halogen, $C_{1-4}$ alkoxy, $C_{1-4}$ haloalkoxy, $OC(=O)R_5$, $C(=O)R_5$, $S(=O)_mR_7$ or $SO_2NR_3R_4$, wherein m is 0–2 and n is 0–2;

$R_3$ and $R_4$ are the same or different and are H; $C_{1-8}$ alkyl; $C_{2-4}$ alkyl substituted optionally with OH, halogen, $C_{1-4}$ alkoxy or $C(=O)R_5$; OH; $C_{1-4}$ alkoxy; $C_{2-4}$ alkoxy substituted optionally with OH, halogen, $C_{1-4}$ alkoxy or $C(=O)R_5$; or $R_3$ and $R_4$ can be joined to form a ring of 5 or 6 atoms selected from O, S, C or N which can be unsubstituted or substituted optionally on carbon with OH, (=O), halogen, $C_{1-4}$ alkoxy, $C(=O)R_5$, $C_{1-6}$ alkyl, $C_{1-6}$ alkyl substituted optionally with OH, halogen, $C_{1-4}$ alkoxy, $C(=O)R_5$ or on nitrogen with $C_{1-4}$ alkoxy, $C(=O)R_5$, $S(=O)_mR_7$, $C_{1-6}$ alkyl or $C_{2-6}$ alkyl substituted optionally with OH, halogen, $C_{1-4}$ alkoxy, $C(=O)R_5$ or on sulfur by $(=O)_m$, wherein m is 0–2;

$R_5$ is $C_{1-8}$ alkyl; $C_{1-4}$ alkyl substituted optionally with OH, $NR_3R_4$, halogen, $C_{1-4}$ alkoxy or $C(=O)R_8$; $C_{1-4}$ alkoxy; $C_{2-4}$ alkoxy substituted optionally with OH, $NR_3R_4$, halogen or $C_{1-4}$ alkoxy; or $NR_3R_4$.

$R_6$ is a monocyclic ring system of 5 or 6 atoms composed of C, N, O and/or S, selected from the group consisting of benzene, furan, thiophene, pyrrole, pyrazole, imidazole, triazole, tetrazole, oxazole, isoxazole, isothiazole, thiazole, thiadiazole, pyridine pyrimidine, pyridazine, and pyrazine;

$R_7$ is $C_{1-4}$ alkyl; $C_{2-4}$ alkyl substituted optionally with OH, $NR_3R_4$, $C_{1-4}$ alkoxy or $C(=O)R_5$; $R_6$ which can be unsubstituted or substituted optionally with OH, $(CH_2)_nNR_3R_4$, halogen, $C_{1-4}$ alkoxy, $C_{1-4}$ haloalkoxy, $C(=O)R_5$, $S(=O)_mC_{1-4}$ alkyl or $SO_2NR_3R_4$; wherein m is 0–2 and n is 0–2; and $R_8$ is $C_{1-4}$ alkyl; $C_{1-4}$ alkoxy; amino, $C_{1-3}$ alkylamino, of di-$C_{1-3}$ alkylamino.

6. The method of claim 5 wherein the compound is selected from the group consisting of:

2-[4-(2-Morpholinoethyl)]-2H-thieno[3,2-e]-1,2,3-thiadiazine-6-sulfonamide 1,1-dioxide; and 2-[4-(2-Morpholinylethyl)]-4-methyl-2H-thieno[3,2-e]-1,2,3-thiadiazine-6-sulfonamide 1,1-dioxide.

\* \* \* \* \*